US007928141B2

(12) United States Patent
Li

(10) Patent No.: US 7,928,141 B2
(45) Date of Patent: Apr. 19, 2011

(54) SYNERGISTIC COMPOSITIONS AND METHODS FOR ENHANCING POTENCY AND/OR FOR PROLONGING THE DURATION OF ACTION OF ANESTHETICS

(76) Inventor: Fuchao Li, Beijing (CN)

( * ) Notice: Subject to any disclaimer, the term of this patent is extended or adjusted under 35 U.S.C. 154(b) by 473 days.

(21) Appl. No.: 12/013,578

(22) Filed: Jan. 14, 2008

(65) Prior Publication Data

US 2008/0112945 A1   May 15, 2008

Related U.S. Application Data

(63) Continuation of application No. PCT/CN2006/001615, filed on Jul. 10, 2006.

(30) Foreign Application Priority Data

Jul. 12, 2005   (CN) .......................... 2005 1 0082789

(51) Int. Cl.
*A61K 31/245* (2006.01)
*A61K 31/167* (2006.01)
*C07C 229/60* (2006.01)
*C07C 237/04* (2006.01)
*C07C 237/14* (2006.01)

(52) U.S. Cl. .......... 514/537; 514/626; 514/613; 560/49; 564/163; 564/168

(58) Field of Classification Search ........................ None
See application file for complete search history.

(56) References Cited

U.S. PATENT DOCUMENTS 5,444,054 A * 8/1995 Garleb et al. .................. 514/54
2003/0175360 A1 * 9/2003 Luzzatti ........................ 424/653

FOREIGN PATENT DOCUMENTS

| CN | 1075081 | * | 8/1993 |
| CN | 1295858 | * | 5/2001 |
| WO | WO00/30630 | * | 6/2000 |
| WO | WO2004/017962 | * | 3/2004 |

OTHER PUBLICATIONS

Machine translation of foreign patent application CN1075081 (pub. date Aug. 1993) downloaded from http://www.sipo.gov.cn/sipo_English/.*
Machine translation of foreign patent application CN1295858 (pub. date May 2001) downloaded from http://www.sipo.gov.cn/sipo_English/.*

* cited by examiner

*Primary Examiner* — Eric S Olson
(74) *Attorney, Agent, or Firm* — Matthias Scholl P.C.; Matthias Scholl

(57) ABSTRACT

Taught is a composition for enhancing potency and/or for prolonging the duration of action of an anesthetic comprising dexamethasone, compound vitamin B, metronidazole, berberine, etamsylate, gentamicin, chymotrypsin, methylene blue trihydrate, and 5% sodium bicarbonate aq. When administered with an anesthetic, the composition shortens the onset time of the anesthetic, and prolongs the duration of anesthesia.

14 Claims, No Drawings

SYNERGISTIC COMPOSITIONS AND METHODS FOR ENHANCING POTENCY AND/OR FOR PROLONGING THE DURATION OF ACTION OF ANESTHETICS

CROSS-REFERENCE TO RELATED APPLICATIONS

This application is a continuation of International Patent Application No. PCT/CN2006/001615 with an international filing date of Jul. 10, 2006, designating the United States, now pending, and further claims priority benefits to Chinese Patent Application No. 200510082789.0, filed on Jul. 12, 2005. The contents of both of these specifications are incorporated herein by reference.

BACKGROUND OF THE INVENTION

1. Field of the Invention

This invention relates to the field of anesthesia, and specifically relates to synergistic compositions and methods for enhancing the activity of and/or for prolonging the duration of action of a local anesthetic.

2. Description of the Related Art

Conventional methods of prolonging the duration of anesthesia during surgeries include higher doses, repetition of doses, and continuous administration. All of these methods, however, may cause severe toxic and other side effects in patients. In addition, these methods are not suitable for post-surgical outpatient pain management. Consequently, much research has been directed towards reducing the anesthetic dose and prolonging the duration of action.

For example, Chinese Pat. No. CN1382443A provides a blowfish toxin whose duration of analgesia can reach about 6 hours. However, the toxicity of the blowfish toxin is over 1000 times higher than that of sodium cyanide which limits its applicability. Chinese Pat. No. CN1065203A provides an anesthetic prepared by adding sodium bicarbonate to a mixture of 1% amethocaine and 2% lidocaine in the proportion of 2-5:10-20, to adjust its pH value to between 7 and 7.2. This formula allegedly prolongs the original anesthesia duration from 48 min to 67 min. Chinese Pat. No. CN1075081A provides a compound gel anesthetic which contains chlorhexidini hydrochloride, dicaine hydrochloride, etamsylate, carboxymethyl cellulose, liquid paraffin and gentamicin sulphate. This preparation allegedly prolongs the original anesthesia duration from about 115 min to about 156 min. However, the duration of anesthesia disclosed in these patents is still insufficient for large surgeries.

The development of compounds and methods for post-operative pain management has also attracted attention. For example, Liu Xiaohong, at the Department of Anesthesiology of Chongqing Qianjiang Development Zone Central Hospital has developed a method of epidural administration for post-operative analgesia. This method comprises injecting 5 mL 0.5% bupivacaine combined with 10 mg dexamethasone by epidural administration and increases the duration of anesthesia to about 11.5 hours.

Nevertheless, certain large surgeries, especially liposuction, requires anesthesia lasting for up to 3 days or longer. Accordingly, it is imperative to develop compositions and methods which can prolong the duration of anesthesia greatly enough to meet with the need of long term analgesia, so as to relieve pain and suffering of patients.

SUMMARY OF THE INVENTION

The invention aims to provide synergistic compositions and methods for enhancing the potency and/or to prolong the duration of action of local anesthetics. In certain composition and methods, these compositions are combined with other surgical anesthetics so as to increase the anesthetic potency and effect and to prolong the duration of anesthesia.

In certain embodiments of the invention, drugs acting on the nervous system have been selected, combined and tested for their potency enhancing and duration of action prolonging characteristics with respect to local anesthetics.

In certain embodiments of the invention, drug compositions were mixed with routine anesthetics (e.g., lidocaine, etc.) and injected subcutaneously, so as to observe a synergistic effect with respect to potency and prolonging of the duration of action of the selected drug composite on routine anesthetics.

In certain embodiments of the invention, a composition for enhancing potency and/or for prolonging the duration of action of an anesthetic comprises: 0.1-100 mg dopamine, 1-200 mg dexamethasone, 0.5-20 mg compound Vitamin B, 10-400 mg metronidazole, 10-1000 mg berberine, 0.5-200 mg etamsylate, 40,000-800,000 U gentamicin, 400-1000 U chymotrypsin, 0.01-80 mg a methylene blue trihydrate, and 0.1-700 mL 5% m/v sodium bicarbonate.

In certain embodiments of the invention, the anesthetic is selected from amucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropivacaine, salicyl alcohol, tetracaine hydrochloride, tolycaine, trimecaine, zolamine, and pharmaceutically acceptable salts thereof. In a class of this embodiment, lidocaine, bupivacaine, or tetracaine are preferred.

In certain embodiments of the invention, the compound vitamin B is composed of Vitamin $B_1$, Vitamin $B_2$, Vitamin $B_6$ and/or Vitamin $B_{12}$ in any proportion of weight, e.g., equal to 10-30:1-4:10-30:40-60.

The synergistic composition for enhancing the potency and/or for prolonging the duration of action of a local anesthetic is a pharmaceutical composition used to combine with surgical anesthetic, which in itself contains no anesthetic components, but does enhance analgesia of the anesthetic with which the composition is administered, shortens its onset time, and significantly prolongs its duration of analgesia.

As for content proportion of each component in this drug composite, except for gentamicin and chymotrypsin which are expressed in standard units, the other components are all indicated in milligrams.

In certain embodiments of the invention, a composition for enhancing potency and/or for prolonging the duration of action of an anesthetic further comprises vitamin C and its weight proportion is smaller that 1 with respect to individual Vitamin B amounts.

As for the anesthetic used to combine with the synergistic composition for enhancing potency and/or for prolonging the duration of action of an anesthetic, its types are not limited. It is, for example, any routine local anesthetic, such as lidocaine, bupivacaine, tetracaine, etc., and so an. An anesthetist may choose a suitable anesthetic according to individual circumstances on his/her own accord.

In addition, the anesthetist also may add 5% w/v aqueous sodium bicarbonate solution according to individual circumstances for injection, which can relieve pain resulting from injection. Meanwhile, according to various demands, other essential additives may be added into the synergistic composition.

Furthermore, the dose of the synergistic composition for enhancing potency and/or for prolonging the duration of action of an anesthetic depends on that of the local anesthetic used and the location and size of operation site.

The dose range of each component refers to the dose combined with anesthetic in a surgery. As a skilled artisan appreciates, the dose of synergistic composition for enhancing potency and/or for prolonging the duration of action of an anesthetic reduces accordingly with that of anesthetic during a small operation or some operation to requires short-time analgesia. On the contrast, during a large operation or any other one to require long-time analgesia, the dose of synergistic composition for enhancing potency and/or for prolonging the duration of action of an anesthetic increases accordingly with increase of anesthetic dose. However, it should be stated that a change in dose is within the scope of this invention.

Although each component of the invention is indicated in mass (mg) or standard units, this is solely to indicate the relation of proportion, but not the absolute quantity relation. For example, even though mass (mg) or standard units of one component or more is not within the scope described above, as long as the proportion between components content complies with that of the above said components, it is within the scope of this invention.

Compared with the existing technologies, this invention has the following advantages:

1. In certain embodiments of the invention, the duration of analgesia can reach from 3 to 9 days or longer.

2. In certain embodiments of the invention, the onset time is comparably shorter so as to relieve pain in patients during an operation.

3. In certain embodiments of the invention, intrathecal mode of administration of anesthesia used in conventional methods is replaced by subcutaneous local administration near operation sites or intramuscular administration, so as to increase greatly safety of anesthesia during operation.

4. In certain embodiments of the invention, the dose of anesthetic is lowered compared to conventional methods as to reduce toxic or side effect of anesthetic.

5. In certain embodiments of the invention, low cost and good effect is achieved. Compounds and methods of this invention are especially suitable for application in hospitals located in remote areas, especially those not equipped with anesthesiologists or anesthetists.

6. In certain embodiments of the invention, compounds and methods of this invention are especially suitable for application in various surgical operations on humans and non-humans (e.g., animals), and in various fields of surgery, such as general surgery, ophthalmology and otorhinolaryngology, stomatology, gynecology, and plastic surgery.

DETAILED DESCRIPTION OF THE INVENTION

Examples

In the following examples, the following abbreviations are used:
L.S.Z.—composition for enhancing potency and/or for prolonging the duration of action of an anesthetic.

Example 1

Single Anesthetic Trial in Small Area Operations

Eyebrow Plucking

The components of the L.S.Z solution and their proportions were:

| | |
|---|---|
| 0.1 mg | dopamine |
| 1 mg | dexamethasone |
| 0.5 mg | compound Vitamin B (proportion of Vitamin $B_1$:Vitamin $B_2$:Vitamin $B_6$:Vitamin $B_{12}$ is 20:2:20:50) |
| 10 mg | metronidazole |
| 10 mg | berberine |
| 0.5 mg | etamsylate |
| 40,000 U | gentamicin |
| 400 U | chymotrypsin |
| 0.01-80 mg | methylene blue trihydrate |
| 0.1-700 mL | 5% w/v sodium bicarbonate |

The above components were dissolved in a small amount (<1 mL) of distilled water and mixed homogeneously, and the mixture was then diluted to 2 mL to yield the L.S.Z. solution.

The L.S.Z. solution was mixed with 2 mL 2% v/v lidocaine solution (a local anesthetic, with a concentration of 2% dissolved in the normal saline solution) to give 4 mL of an L.S.Z. anesthetic solution having a long duration of action.

Then, a common syringe with a 3 cm long needle was used to inject subcutaneously the above anesthetic solution into the eyebrow area. The 4 mL of the anesthetic solution was entirely injected into three injection points in each eyebrow area, with a subcutaneous injection depth of about 0.5 cm.

The anesthetic began to take effect 5 min. after the injection, and the duration of analgesia was about 9 days.

Example 2

Anesthetic Trial in Middle Area Operations

Liposuction in the Abdomen

The components of the L.S.Z solution and their proportions were:

| | |
|---|---|
| 50 mg | dopamine |
| 100 mg | dexamethasone |
| 10 mg | compound Vitamin B (proportion of Vitamin $B_1$:Vitamin $B_2$:Vitamin $B_6$:Vitamin $B_{12}$ is 20:2:20:50) |
| 100 mg | metronidazole |
| 500 mg | berberine |
| 100 mg | etamsylate |
| 400,000 U | gentamicin |
| 700 U | chymotrypsin |
| 25 mg | methylene blue trihydrate |
| 150 mL | 5% w/v sodium bicarbonate |

The above components were dissolved in a small amount (<1 mL) of distilled water and mixed homogeneously, and the mixture was then diluted to 10 mL to yield the L.S.Z. solution.

10 bottles were filled each with 500 mL of normal saline solution. To each bottle was added 10 ml 2% lidocaine solution (as described in Example 1), and 1 mL of the L.S.Z. solution. The bottles were shaken respectively to mix well, yielding L.S.Z. anesthetic solution having a long duration of action.

Then, a common syringe with a 20 cm long needle long was used to inject subcutaneously the above anesthetic solution into the abdomen area of a female, 1.62 m in height, and 63 kg weight. While injecting the anesthetic solution, liposuction was conducted using a liposuction tube, finally removing 3500 mL aspirated fat solution in total. The operation lasted 1 hour. When injecting, 3 injection points, the subcutaneous depth of 1-2 cm, and radiation injection around the injection point were chosen to form 3 anesthetic zones with a radius of 15 cm. After injection, the onset time shortened from the original about 1 min (using only lidocaine) down to about 5 sec, and the duration of analgesia prolonged from the original 4 hours (using only lidocaine) to about 9 days.

These results suggest that in certain embodiments of the present invention, the L.S.Z solution could shorten the onset time for local anesthetic notably, and could prolong the duration of analgesia more than 50 times.

It should be stated that the dose of the anesthetic solution with long-term effect may be increased or decreased appropriately with the quantity of liposuction that is desired.

Example 3

Anesthetic Trial in Large Area Operations
Liposuction in the Lower Limb, Including Buttock, Thigh and Calf The components of the L.S.Z solution and their proportions were:

| | |
|---|---|
| 100 mg | dopamine |
| 200 mg | dexamethasone |
| 20 mg | compound Vitamin B (proportion of Vitamin $B_1$:Vitamin $B_2$:Vitamin $B_6$:Vitamin $B_{12}$ is 20:2:20:50) |
| 350 mg | metronidazole |
| 1000 mg | berberine |
| 200 mg | etamsylate |
| 800,000 U | gentamicin |
| 1000 U | chymotrypsin |
| 40 mg | methylene blue trihydrate |
| 300 mL | 5% w/v sodium bicarbonate |

The above components were dissolved in a small amount (<1 mL) of distilled water and mixed homogeneously, and the mix was then diluted to 60 mL to yield the L.S.Z. solution.

20 bottles were filled each with 500 mL normal saline solution. To each bottle was added 15 mL of 2% lidocaine solution (as described in Example 1) and 3 mL of the L.S.Z. solution as prepared in this Example. The bottles were shaken respectively to mix well, yielding L.S.Z. anesthetic solution having a long duration of action.

Then, a common syringe with a 25 cm long needle was used to inject subcutaneously the above anesthetic solution in the buttock, the thigh and the calf of a female, 1.65 m in height, and 65 kg in weight. While injecting the anesthetic solution, liposuction was conducted using a liposuction tube, finally removing 6 L aspirated fat solution in total. The operation lasted for about 3 hours. When injecting, 8 injection points, the subcutaneous depth of 1-2 cm, and the radiation injection method around the injection point were chosen to form 8 anesthetic zones with a radius of 20 cm. After injection, the onset time shortened from the original about 1 min (using only lidocaine) down to around 5 sec, and the duration of analgesia prolonged from the original 4 hours (using only lidocaine) to about 9 days.

These results suggest that in certain embodiments of this invention, the L.S.Z solution could shorten the onset time for local anesthetic notably, to as short as one-twelfth of the original time, and could prolong the duration of analgesia more than 50 times.

Example 4

Anesthetic Trial in General Liposuction Operations

The components of the L.S.Z solution and their proportions were:

| | |
|---|---|
| 100 mg | dopamine |
| 200 mg | dexamethasone |
| 20 mg | compound Vitamin B (proportion of Vitamin $B_1$:Vitamin $B_2$:Vitamin $B_6$:Vitamin $B_{12}$ is 20:2:20:50) |
| 350 mg | metronidazole |
| 1000 mg | berberine |
| 200 mg | etamsylate |
| 800,000 U | gentamicin |
| 1000 U | chymotrypsin |
| 40 mg | methylene blue trihydrate |
| 300 mL | 5% w/v sodium bicarbonate |

The above components were dissolved in a small amount (<1 mL) of distilled water and mixed homogeneously, and the mix was then diluted to 150 mL to yield the L.S.Z. solution.

50 bottles were filled each with 500 mL normal saline solution. To each bottle was added 15 mL of 2% lidocaine solution (as described in Example 1) and 3 mL of the L.S.Z. solution as prepared in this Example. The bottles were shaken respectively to mix well, yielding L.S.Z. anesthetic solution having a long duration of action.

Then, a common syringe with a 25 cm long needle was used to inject subcutaneously the above anesthetic solution in 45 sites of a female, 1.70 m in height, and 90 kg in weight. While injecting the anesthetic solution, liposuction was conducted using a liposuction tube, finally removing 18 L aspirated fat solution in total. The operation lasted for about 9 hours and the weight of the subject was reduced by 15 kg in total.

After injection, the onset time shortened from the original about 1 min (using only lidocaine) down to around 5 sec, and the duration of analgesia prolonged from the original 4 hours (using only lidocaine) to about 9 days.

Example 5

Caesarian Section

Except for the anesthetic, which was 50 mL 0.25% bupivacaine and 10 mL 5% sodium bicarbonate, the other components were the same as described in Example 1. The results indicated that the onset time was 5 sec and the duration of analgesia was over 9 days.

Example 6

Appendectomy

The anesthetic and the composition for enhancing potency and/or for prolonging the duration of action of the anesthetic used in this example were as same as those in Example 5. The results revealed that the onset time was 5 sec and the duration of analgesia was over 9 days.

Example 7

Lower Jaw Augmentation

Except for the anesthetic, which was 20 mL 2% tetracaine and 5 mL 5% sodium bicarbonate, the other components were the same as described in Example 1. The results indicated that the onset time was 5 sec and the duration of analgesia was over 3 days.

Example 8

Vaginal Tightening Surgery

The anesthetic and the composition for enhancing potency and/or for prolonging the duration of action of the anesthetic used in this example were as same as described in Example 7. The results revealed that the onset time was 5 sec and the duration of analgesia was over 3 days.

Similar trials to those described in Examples 1-8 were undertaken more widely and all have achieved satisfying effects. For example surgeries conducted in Kunming Hospital of Plastic Specialty, Beijing Huangsi Hospital, Navy General Hospital and other many beauty surgery departments of large plastic hospitals across China included 167 cases of liposuction operations, 93 cases of breast augmentations operations, 81 cases of nose operations, 129 cases of double-eyelid surgeries, 12 cases of eyelash cutting operations, 45 cases of pouch operations, and 17 cases of mandible angle ostectomy operations, in all of which, the satisfying effect were achieved.

In addition, in Navy General Hospital, the composition for enhancing potency and/or for prolonging the duration of action of the anesthetic was used in surgical outpatient and inpatient operations of over 20 cases in total for appendicitis, atheromatosis, phimosis, breast tumor, and so on. All these operations all achieved good effect of analgesia and a longer and satisfying duration of analgesia.

Furthermore, promotion of wide application of embodiments of this invention was conducted in various regions of China. In total more than 6000 cases of related trials were performed, and all achieved satisfying effect, with no failure or no toxic or other side effects.

It should be stated that, while performing a surgery, skilled artisans may deviate from the exact description of the embodiments of this invention, for example by adding proper quantity of 5% sodium bicarbonate so as to relieve the pain sense at the beginning of injection. These measures themselves do not belong to scope of this invention, and hence were not described in detail herein. Surgeons may take some measures essential for a surgery according to the formula of this invention and encountered circumstances. However, as long as the components and the proportion scope used by a surgeon complies with those listed in the technological strategy of this invention, they all belong to the scope of this invention.

The composition for enhancing potency and/or for prolonging the duration of action of the anesthetic in this invention allows for the duration of analgesia reach 3-9 days or longer; it shortens the onset time for anesthetic; in most cases, alters the administration method for anesthesia from intrathecal mode of administration used conventionally to subcutaneous local administration near operation sites or intramuscular administration; reduces the dose of anesthetic; leads to lower cost without compromising therapeutic effects; and is applied widely to various surgeries in the humans and animals in the fields of general surgery, ophthalmology, otolaryngology, stomatology, gynecology, plastic surgery, etc.

The term "duration of action" refers herein to the length of time an anesthetic exhibits a desired pharmacologic effect after administration. This is determined by the amount of time drug concentration is at or above the minimum effective concentration. The duration of drug in the body is not equivalent to the duration of effect. A drug may be in the body for a period of time that is much longer than the duration of action, if the concentration remains below the minimum effective concentration. In fact, some drugs that are slowly absorbed may never exert a pharmacologic effect, even though they are in the body for a prolonged period of time. This occurs when the drug is absorbed so slowly that it never reaches concentrations that meet or exceed the minimum effective concentration.

The term "prolonging," as used herein with respect to the duration of action, refers to the increase in the length of time an anesthetic exhibits a desired pharmacologic effect after administration in combination with a duration-of-action-prolonging agent or composition.

The term "potency" is generally a comparison measure of the relative concentration of an anesthetic required to achieve a given magnitude of response (e.g., anesthesia). This comparison is often made by determining the concentration necessary to produce 50% of the maximal effect ($EC_{50}$) for both compounds. The compound with the lower EC50 is the more potent compound. When the concentration response curve for a drug shifts to the right, it is an indication that the potency has decreased. This can happen in disease states where the target organ becomes less responsive to the drug, such that more drug is needed to achieve a given response.

The term "increased", as used herein with respect to potency, refers to the decrease in the relative concentration of an anesthetic required to achieve a given magnitude of response when administered in combination with a duration-of-action-prolonging agent or composition, compared to the relative concentration of an anesthetic required to achieve a given magnitude of response when administered alone.

This invention is not to be limited to the specific embodiments disclosed herein and modifications for various applications and other embodiments are intended to be included within the scope of the appended claims. While this invention has been described in connection with particular examples thereof, the true scope of the invention should not be so limited since other modifications will become apparent to the skilled practitioner upon a study of the drawings, specification, and following claims.

All publications and patent applications mentioned in this specification are indicative of the level of skill of those skilled in the art to which this invention pertains. All publications and patent applications mentioned in this specification are herein incorporated by reference to the same extent as if each individual publication or patent application mentioned in this specification was specifically and individually indicated to be incorporated by reference.

What is claimed is:

1. A composition for enhancing potency and/or for prolonging the duration of action of an anesthetic comprising dexamethasone, a vitamin B, metronidazole, berberine, etamsylate, gentamicin, chymotrypsin, methylene blue trihydrate, and sodium bicarbonate, wherein the components are provided in the following amounts per unit of the composition: dopamine—0.1-100 mg, dexamethasone—1-200 mg, vitamin B—0.5-20 mg, metronidazole—10-400 mg, berberine—10-1000 mg, etamsylate—0.5-200 mg, gentamicin—40,000-800,000 U, chymotrypsin—400-1000 U, methylene blue trihydrate—0.01-80 mg, 5% w/v sodium bicarbonate aq. 0.1-700 mL.

2. The composition of claim 1 wherein vitamin B is a mixture of Vitamin $B_1$, Vitamin $B_2$, Vitamin $B_6$, and Vitamin $B_{12}$ provided in any weight proportion.

3. A composition for enhancing potency and/or for prolonging the duration of action of an anesthetic comprising dexamethasone, a vitamin B, metronidazole, berberine, etamsylate, gentamicin, chymotrypsin, methylene blue trihydrate, and sodium bicarbonate, wherein vitamin B is a mixture of Vitamin $B_1$, Vitamin $B_2$, Vitamin $B_6$, and Vitamin $B_{12}$, and the weight proportion of Vitamin $B_1$ to Vitamin $B_2$ to Vitamin $B_6$ to Vitamin $B_{12}$ is 10-30:1-4:10-30:40-60.

4. An anesthetic composition comprising a local anesthetic, dexamethasone, a vitamin B, metronidazole, berberine, etamsylate, gentamicin, chymotrypsin, methylene blue trihydrate, and sodium bicarbonate, wherein vitamin B is a mixture of Vitamin $B_1$, Vitamin $B_2$, Vitamin $B_6$, and Vitamin $B_{12}$, and the weight proportion of Vitamin $B_1$ to Vitamin $B_2$ to Vitamin $B_6$ to Vitamin $B_{12}$ is 10-30:1-4:10-30:40-60.

5. The anesthetic composition of claim 4 wherein the local anesthetic is selected from lidocaine, bupivacaine, or tetracaine.

6. A method for enhancing potency and/or for prolonging the duration of action of an anesthetic comprising administering to a patient in addition to the anesthetic, a composition comprising dexamethasone, a vitamin B, metronidazole, berberine, etamsylate, gentamicin, chymotrypsin, methylene blue trihydrate, and sodium bicarbonate, wherein vitamin B is a mixture of Vitamin $B_1$, Vitamin $B_2$, Vitamin $B_6$, and Vitamin $B_{12}$, and the weight proportion of Vitamin $B_1$ to Vitamin $B_2$ to Vitamin $B_6$ to Vitamin $B_{12}$ is 10-30:1-4:10-30:40-60.

7. The method of claim 6 wherein the local anesthetic is selected from lidocaine, bupivacaine, or tetracaine.

8. An anesthetic composition comprising a local anesthetic, dexamethasone, a vitamin B, metronidazole, berberine, etamsylate, gentamicin, chymotrypsin, methylene blue trihydrate, and sodium bicarbonate, wherein the components are provided in the following amounts per unit of the composition: dopamine—0.1-100 mg, dexamethasone—1-200 mg, vitamin B—0.5-20 mg, metronidazole—10-400 mg, berberine—10-1000 mg, etamsylate—0.5-200 mg, gentamicin—40,000-800,000 U, chymotrypsin—400-1000 U, methylene blue trihydrate—0.01-80 mg, 5% w/v sodium bicarbonate aq. 0.1-700 mL.

9. The anesthetic composition of claim 8 wherein the local anesthetic is selected from lidocaine, bupivacaine, or tetracaine.

10. The composition of claim 8 wherein vitamin B is a mixture of Vitamin $B_1$, Vitamin $B_2$, Vitamin $B_6$, and Vitamin $B_{12}$, and the weight proportion of Vitamin $B_1$ to Vitamin $B_2$ to Vitamin $B_6$ to Vitamin $B_{12}$ is 10-30:1-4:10-30:40-60.

11. A method for enhancing potency and/or for prolonging the duration of action of an anesthetic comprising administering to a patient in addition to the anesthetic, a composition comprising dexamethasone, a vitamin B, metronidazole, berberine, etamsylate, gentamicin, chymotrypsin, methylene blue trihydrate, and sodium bicarbonate, wherein the components are provided in the following amounts per unit of the composition: dopamine—0.1-100 mg, dexamethasone—1-200 mg, vitamin B—0.5-20 mg, metronidazole—10-400 mg, berberine—10-1000 mg, etamsylate—0.5-200 mg, gentamicin—40,000-800,000 U, chymotrypsin—400-1000 U, methylene blue trihydrate—0.01-80 mg, 5% w/v sodium bicarbonate aq. 0.1-700 mL.

12. The method of claim 11 wherein the local anesthetic is selected from lidocaine, bupivacaine, or tetracaine.

13. The method of claim 11, wherein vitamin B is a mixture of Vitamin $B_1$, Vitamin $B_2$, Vitamin $B_6$, and Vitamin $B_{12}$, and the weight proportion of Vitamin $B_1$ to Vitamin $B_2$ to Vitamin $B_6$ to Vitamin $B_{12}$ is 10-30:1-4:10-30:40-60.

14. The composition of claim 1 wherein vitamin B is a mixture of Vitamin $B_1$, Vitamin $B_2$, Vitamin $B_6$, and Vitamin $B_{12}$, and the weight proportion of Vitamin $B_1$ to Vitamin $B_2$ to Vitamin $B_6$ to Vitamin $B_{12}$ is 10-30:1-4:10-30:40-60.

* * * * *